United States Patent

Wagner et al.

[11] Patent Number: 5,507,815
[45] Date of Patent: Apr. 16, 1996

[54] RANDOM SURFACE PROTRUSIONS ON AN IMPLANTABLE DEVICE

[75] Inventors: Donald J. Wagner, Venetia; Gary Reed, Clairton, both of Pa.

[73] Assignees: Cycam, Inc., Houston; Tech Met, Inc., Glassport, both of Pa.

[21] Appl. No.: 358,045

[22] Filed: Dec. 15, 1994

Related U.S. Application Data

[63] Continuation of Ser. No. 122,254, Sep. 15, 1993, abandoned, which is a continuation of Ser. No. 716,167, Jun. 17, 1991, abandoned.

[51] Int. Cl.⁶ .................... A61F 2/28; A61F 2/30
[52] U.S. Cl. .................... 623/16; 623/11; 623/18; 623/66
[58] Field of Search .................... 623/66, 901, 16, 623/11, 12, 18, 19, 20, 22, 23; 427/2

[56] References Cited

U.S. PATENT DOCUMENTS

| | | |
|---|---|---|
| 3,650,861 | 3/1972 | Angell . |
| 3,891,456 | 6/1975 | Hohman et al. . |
| 3,995,371 | 12/1976 | O'Keefe ........................ 32/15 |
| 4,116,755 | 9/1978 | Coggins et al. . |
| 4,272,855 | 6/1981 | Frey . |
| 4,314,876 | 2/1982 | Kremer et al. . |
| 4,330,891 | 5/1982 | Branemark et al. . |
| 4,414,039 | 11/1983 | Thoma . |
| 4,540,465 | 9/1985 | Coggins et al. . |
| 4,588,480 | 5/1986 | Thoma . |
| 4,644,942 | 2/1987 | Sump . |
| 4,673,409 | 6/1987 | Van Kampen . |
| 4,803,098 | 2/1989 | Henri et al. . |
| 4,834,756 | 5/1989 | Kenna . |
| 4,836,884 | 6/1989 | McAuslan . |
| 4,846,837 | 7/1989 | Kurze et al. . |
| 4,863,475 | 9/1989 | Andersen et al. . |
| 4,865,603 | 9/1989 | Noiles . |
| 4,900,398 | 2/1990 | Chen . |
| 4,944,763 | 7/1990 | Willert et al. . |
| 4,955,909 | 12/1990 | Ersek et al. . |
| 4,978,358 | 12/1990 | Bobyn ........................ 623/23 |
| 5,002,572 | 3/1991 | Picha . |
| 5,002,580 | 3/1991 | Noble et al. . |
| 5,158,571 | 10/1992 | Picha . |
| 5,246,530 | 9/1993 | Bugle et al. ........................ 156/643 |

Primary Examiner—David J. Isabella
Attorney, Agent, or Firm—Barry I. Friedman; Dickie, McCamey & Chilcote

[57] ABSTRACT

An attachment surface for an implantable device has a random irregular pattern formed through a repetitive masking and chemical milling process. Surface material is removed from the implant surface without stress on the adjoining material and the process provides fully dimensional fillet radii at the base of the surface irregularities. This irregular surface is adapted to receive the ingrowth of bone material and to provide a strong anchor for that bone material. The unitary nature of the substrate and surface features provides a strong anchoring surface with is resistant to cracking or breaking. The surface is prepared through an etching process which utilizes the random application of a maskant and subsequent etching of the metallic substrate in areas unprotected by the maskant. This chemical etching process is repeated a number of times as necessitated by the nature of the irregularities required in the surface. The etching characteristics are controlled by the time, temperature and number of repetitions utilized in the etching process.

20 Claims, 2 Drawing Sheets

RANDOM SURFACE PROTRUSIONS ON AN IMPLANTABLE DEVICE

CROSS REFERENCE TO RELATED APPLICATION

This application is a continuation of Wagner, et al., similarly titled, bearing Ser. No. 122,254, filed Sep. 15, 1993, now abandoned, which was a continuation of Wagner, et al., Ser. No. 716,167, filed Jun. 17, 1991, also now abandoned.

BACKGROUND OF THE INVENTION

1. Field of the Invention

The present invention relates to an irregular surface which is utilized on a bone implant to facilitate the growth of bone tissue within the surface. The invention also relates to a method of production of this surface. More specifically, the invention relates to the sequential etching of a bone implant surface to produce an irregular random pattern of protrusions and depressions through the use of chemical milling techniques.

2. Description of the Prior Art

In the field of bone implantation, or the use of man-made objects to replace portions of bone within the human body, there are two primary methods of affixing the implant device to the existing bone. The first of these methods involves the use of a cement or adhesive material which is applied to the surfaces of the implant and the bone. The cement is adapted to harden in a rapid fashion and rigidly affix the two portions in an immobile manner. The use of cement permits the application of loads to the joiner of the bone and the implant within a relatively short time following implantation. This is generally desirable in terms of the well-being of the patient, in that a quick physical recovery improves the overall recovery of the patient.

One of the significant shortcomings of a cement adhesion of the two elements is that over time, the cement tends to deteriorate. This deterioration may permit relative movement between the implant and the bone surface and if untreated, could allow the two joined elements to separate. In either event, the result is painful and dangerous to the patient.

A second method of affixation of the implant to the bone has also been utilized as an alternative to the cement technique. In this embodiment, the implant is provided with an irregular surface into which the bone may grow, creating a natural joiner between the bone and the implant. One of the shortcomings of this implantation technique, however, is the longer recovery time necessary to permit ingrowth of the bone into the surface of the implant. An additional problem which has occurred with relation to the ingrowth embodiment relates to the preparation of the surface of the implant. An implant having a smooth surface is inappropriate for use in this type of operation as it provides no gripping surface for the bone. An irregular surface, therefore, is preferred and in fact necessary for this application. Several methods have been proposed in the prior art for the preparation of the surface, such that a stable gripping surface will be provided into which the bone may grow.

Frye, U.S. Pat. No. 4,272,855, issued Jun. 16, 1981, discloses the use of generally conical projections emanating from the surface of the implant. These projections may be perpendicular to the surface of the implant or may be extending outwardly at an angle between 50° and 90°, with respect to the surface of the implant. Frye teaches that an increase in the anchoring surface is a decisive feature which can influence and improve the bond between tissue and the implant. The projections described in Frye are generally regular in shape and devoid of corners and edges and have transition surfaces merging into the base level.

Van Kampen, U.S. Pat. No. 4,673,409, issued Jun. 16, 1987, discloses an implant having a surface comprising a multiplicity of spaced posts projecting from the implant surface for mating with bone material. The Van Kampen reference specifically teaches away from an edgeless surface as taught by the Frye reference. Van Kampen instructs that while a rounded surface minimizes the formation of stresses, it minimizes the total surface area that may be joined to the tissue, thus reducing the strength of the implant. Van Kampen discloses the use of regular posts which are roughly rectangular in cross-section. The posts are spaced at a regular interval and are formed by laser drilling.

It is evident from the teaching of these two references that there is some disagreement in the art regarding the best approach towards the preparation of an implant surface.

Another technique in the preparation of an implant surface is disclosed in Sump, U.S. Pat. No. 4,644,942, issued Feb. 24, 1987. The Sump reference discloses the use of a coating which is applied to the surface of the implant. The coating is comprised of a solid metallic powder and a solution of organic binders. A slurry formed of the two elements is applied to the surface of the implant and is permanently affixed thereto under controlled temperature and pressure conditions. The organic material is subsequently removed, leaving a porous, metallic coating on the surface of the implant.

Other techniques for applying a similar coating include plasma spray of a metallic material onto the surface of an implant resulting in a similar metallic irregular coating. While these porous coatings do provide an attachment surface into which bone may grow, these surfaces and the surface described in Noiles, U.S. Pat. No. 4,865,603, issued Sep. 13, 1989, exhibit significant shortcomings. The Noiles reference describes a surface in which furrows and depressions are cut or stamped into the surface of the implant. Each of these surfaces involves the addition of metallic material or the manipulation of the metallic surface of the implant. Each of these methodologies provides a surface that is subject to breakage and dislocation under stress. A metallic addition to the surface of the implant, even under rigorously controlled conditions, forms a joiner which is more easily broken than a singularly formed piece of metallic substrate. Similarly, the manipulation of the surface of the implant, even though formed of a single integral metal substrate, involves the stressing of the metallic surface which forms a locus for breakage when the implant is under a load.

What is lacking in the art, therefore, is an attachment surface utilized in conjunction with a metallic bone implant which has the structural integrity of a unitary element formed without the necessity of stressing that surface through manipulation. Additionally, what is needed in the art is a surface having the irregularities provided by an applied coating without the necessary lack of strength inherent in the joiner of the coating material to the implant substrate.

SUMMARY OF THE INVENTION

An attachment surface is provided in which a random irregular pattern is formed through a repetitive masking and chemical milling process. Surface material is removed from the implant without stress on the adjoining material, and the process provides fully dimensioned fillet radii at the base of the surface irregularities which is then adapted to receive the ingrowth of bone material when joined to bone during implantation. An irregular series of projections and depressions is formed to accommodate such ingrowth, providing a large surface area without any surface manipulations or additions.

The surface is prepared through an etching process which utilizes the random application of a maskant and subsequent etching of the metallic substrate in areas unprotected by the maskant. This etching process is repeated a number of times as necessitated by the amount and nature of the irregularities required for any particular application. Control of the strength of the etchant material, the temperature at which the etching process takes place and the time allotted for such an etching technique permit fine control over the resulting surface produced by the process. The number of repetitions of the etching process is also utilized to control the surface features.

The particular maskant and etchant utilized for a given attachment surface is dictated by the base metal utilized for the implant. While a titanium implant is contemplated as the best mode of practice in the invention, it is to be specifically understood that any base metal may be utilized as the implanted material. A change in the base metal would necessitate a change in the maskant and etchant. No limitation is to be inferred from the selection of titanium in the detailed description following nor in the selection of the particular maskant and etchant chemistries.

These and other advantages and features of the present invention will be more fully understood upon reference to the presently preferred embodiments thereof and to the appended drawings.

DESCRIPTION OF THE PREFERRED EMBODIMENTS

Figure 1:
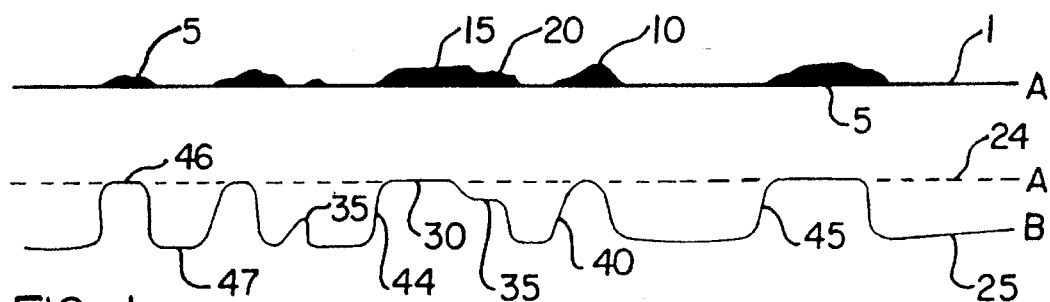
FIG. 1 is a diagrammatic representation of a first cycle of the etching process, illustrating a first surface having a maskant applied thereto and a second surface indicating the resultant surface after etching.

In describing the preferred embodiment of the invention and the best mode of carrying the invention out, the drawings and description refer to the use of a titanium alloy base metal. While titanium is the preferred embodiment for the implantable material, a number of other alloys may be utilized. Each of these different alloys will require a different maskant and etchant composition. While no specific details are given in the specification regarding the use of these other metals and etchants, it is considered to be well within the knowledge of an experienced practitioner in the art to select an etchant once a base alloy has been identified. Furthermore, for the purposes of clarity, certain repetitive elements in the drawings have not been numerically identified for each and every occurrence. For example, a number of maskant points are shown on the surface diagrams. It is considered apparent from the drawings that the maskant points and other surface features of the etched implant are repeated and are readily identifiable without the aid of numeric identification for each feature. Only representative features and maskant points have therefore been identified.

Referring now to FIG. 1, an unfinished surface 1 is provided which diagrammatically represents the exterior surface of the device to be implanted. The letter identifiers on the right margin of the drawings are intended to provide a quick reference to the relative levels of etching. Unfinished surface 1 at level A is generally smooth and comprised of titanium metal or alloy such as Ti—6Al—4Va. A cobalt chromium alloy is also contemplated. A maskant is applied to the surface of the implant which is to be etched in a random fashion. Several methods may be utilized to accomplish the random spattering of the maskant on the surface. Among these are manually applying the maskant by brushing it using the tips of a hair-type brush or utilizing any type of shredded hair-like fibrous applicator dipped in the maskant material. Another method of application would be delivered in an air stream utilizing an air brush or paint gun.

The maskant must be chosen carefully in order to provide a substance which will cling tightly to the surface of the implant during manipulation of the implant and will also remain stable when the etchant solution is applied to the coated part. The maskant must also be removed with no residue once its function has been accomplished. A particular problem encountered when utilizing maskants is the performance of the maskant at the boundaries of its application. The maskant should produce a sharply defined edge once the etching process has begun and not itself deteriorate during the etching process. This might permit partial degradation of the substrate in a masked area. It should be noted, however, that some deterioration is found in any maskant use and does provide some of the particular surface features of the etched implant described later.

The surface 1 of the implant must be clean and grease-free and any oxidized material should be removed before the application of the maskant. This may be accomplished either mechanically, chemically or both. The surface may be cleaned mechanically utilizing a light abrasive blast of aluminum oxide particles or glass beads. Alternatively, blasting with any small solid particle which will not degrade the surface is contemplated. A chemical agent such as methanol may be utilized alone or in conjunction with the blasting. Most maskants are very sensitive to the condition of the applied surface and both application and removal of the maskant may be affected by improper surface treatment. The maskant can be comprised of a number of materials including neoprene elastomers and isobutylene isoprene copolymers. The particular maskant should be selected based on the type of etchant utilized. The preferred maskant is AC-818C, an air-cured, general purpose, peelable coating produced by A. C. Products, Inc. of Placentia, Calif. The maskant is thinned utilizing perchlorethylene to 35–45 seconds utilizing an No. 5 Zahn cup. The maskant, if too thin, may be thickened to this viscosity by evaporation of the carrier. While the maskant is traditionally utilized in the 14–18 second range, it has been found that this thicker version produces superior results in terms of applying the maskant utilizing manual daubing or spray application techniques. It is to be specifically noted that the maskant is applied in a random spattered fashion allowing only a portion of the surface of the implant to be coated thereby. A random "polka dot" pattern is preferred in which each of the maskant points is of varying size and thickness when compared to the others. In some instances, the applied maskant may be partially abraded utilizing the grit blasting technique described previously for cleaning with an 80–120 mesh grit at 80–90 psi. to assist in providing an irregular maskant coating.

As shown in FIG. 1, a variety of applied maskant points 5 are illustrated. A particularly thick maskant agglomeration 10 is also illustrated. Other surface features of the applied maskant include an applied maskant plateau 15 and an applied maskant thin layer 20. It is desirable to achieve a variety of sizes and thicknesses of maskant in order to obtain the proper random finished surface. As will be seen later, each of these particular maskant surface features produces a somewhat different etched result. An optional step of drying the maskant at an elevated temperature is also contemplated. Four to five minutes at 200° F. is sufficient.

Referring now to the second illustration of FIG. 1, the etched result is illustrated, based on the applied maskant shown in the upper illustration. The unfinished surface indication line 24, shown as a chain, indicates the original level identified by the letter A at which the surface began. The first etched surface 25 identified by the letter B shows the resultant etched surface. While a number of etchants could be utilized, the particular chemistry adopted for the preferred embodiment utilizes a standard 30% nitric acid - 6% hydrofluoric acid combination which is commonly marketed and well known in the art. The etchant is applied at 110° F. for approximately 4 minutes to achieve a desired 0.008–0.010 inch etch depth. This time period or the strength of the etchant solution may be adjusted upwardly or downwardly to achieve a heavier or lighter etching. The etching is halted in a water bath or spray.

The maskant material may be removed in a variety of ways. The material may be removed mechanically or chemically. Depending on the size and number of coated objects, mechanical brushing or blasting of the maskant will peel it off. Additionally, the use of nitric acid is contemplated to dissolve the maskant material.

Referring again to the second illustration of FIG. 1, a number of surface features may be identified. A primary plateau 30 corresponds to the applied maskant plateau 15 illustrated in the top drawing. The heavy maskant coat completely protects the implant surface, preventing any metallic material from being removed at this point. A secondary plateau 35 corresponds to the thin layer 20 illustrated in the above drawing. The intermediate height of the secondary plateau between levels A and B indicates that the maskant performed for some period during the etching cycle but failed at an intermediate time allowing some of the alloy to be etched away. A small promontory, third from the left as shown in FIG. 1, also illustrates a small secondary plateau 35. Gradually sloped feature 40 corresponds to a gradually tapering maskant coverage which partially protects the underlying substrate during the etching cycle. A highly sloped feature 44 indicates a thicker maskant coating which enjoyed a highly defined perimeter before etching. A medium sloped feature 45 indicates a maskant condition intermediate the two previously described. The extremes of the etching are indicated by unetched level 46 and first etched level 47 which illustrate the effect of complete maskant coating versus no maskant coating. It should be noted that the base of each surface feature provides full dimensionally filleted radii.

Figure 2:
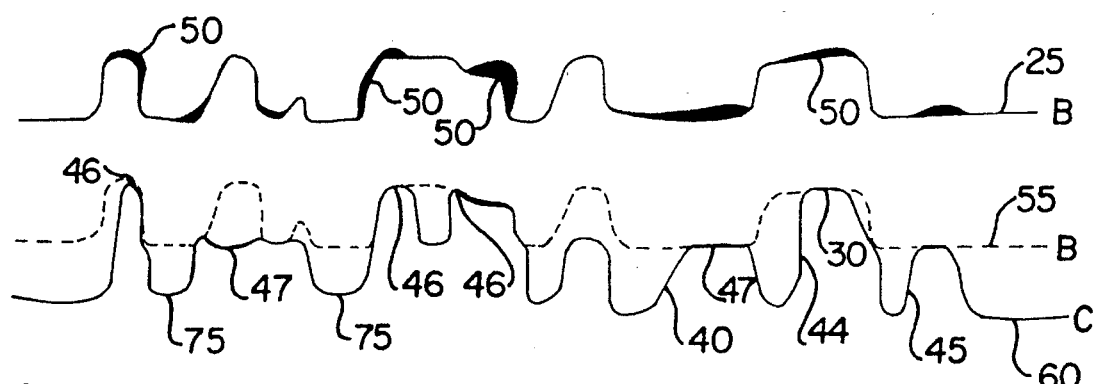
FIG. 2 is a diagrammatic representation of the second cycle of the etching process, illustrating the second surface illustrated in FIG. 1 having a maskant applied thereto and a resultant third surface prepared by etching the masked second surface.

FIG. 2 also employs two illustrations to display the effects of a second masking/etching cycle. The upper illustration corresponds to the second illustration of FIG. 1, the lowest extreme being found at the level indicated as B. The maskant is again applied to a clean and prepared surface in a random fashion according to the same techniques described with reference to FIG. 1. As before, a randomized pattern is preferable in which a wide variety of maskant surface features is achieved. Second applied maskant points 50 illustrate a variety of positions in which the maskant may be applied to the now irregular surface features of first etched surface 25.

Moving to the second illustration of FIG. 2, the first etched surface indication line 55 is shown in chain line to indicate the previous surface prior to the second etching cycle. The second etching cycle is performed under identical conditions as that described with reference to FIG. 1 to again achieve a 0.008–0.010 inch maximum etch. Second etched surface 60 is shown at level C, indicating a resultant etched surface. As previous described, the number of surface features are illustrated corresponding to the characteristics of the applied maskant. A highly sloped surface feature 44 corresponds again to a sharply defined and relatively thick application of maskant while a gradually sloped surface feature 40 corresponds to a gradually thinning maskant application. This feature is particularly visible in the two illustrations contained in FIG. 2 in which the gradual thinning of the maskant application is particularly exaggerated.

As can be seen in the second illustration of FIG. 2, three major levels of surface features are illustrated with a few intermediate features present to demonstrate the effects of partial maskant failure. A few points remain at unetched level 46 indicating maskant coverage during both etchant cycles. Some points are illustrated at first etched level 47 indicating maskant coverage during one of the two cycles, while points located at second etched level 75 have been exposed to the etchant during both of the etching cycles. The increasing level of complexity of surface forms is apparent with comparison between FIGS. 1 and 2.

Figure 3:
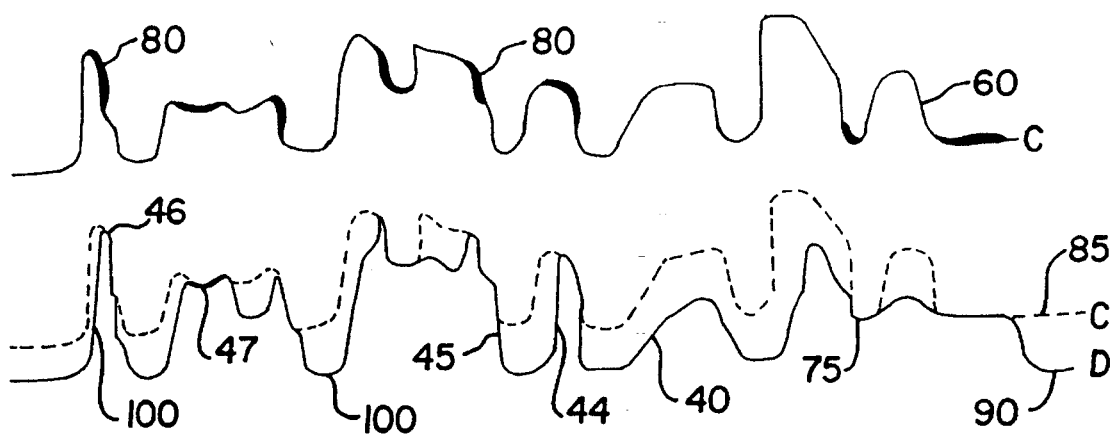
FIG. 3 is a diagrammatic representation of the third cycle of the etching process illustrating the resultant third etched surface of FIG. 2, also having a maskant applied thereto and a fourth surface prepared by etching the masked surface.

FIG. 3 is essentially a repetition of FIG. 2 having an upper illustration showing the application of third applied maskant points 80 to the now highly featured second etched surface 60 at level C. The increasing complexity of the surface of the etched device contributes also to the complexity of the maskant forms when applied to the irregular surface. The second illustration of FIG. 3 is shown to demonstrate the effect of a less rigorous etching cycle, being roughly one-half of the depth shown in FIGS. 1 and 2. The number and length of each etching cycle is purely dependent on the complexity of features required by the application and may be performed by any order. As shown in the second illustration of FIG. 3, a gradually sloped surface feature 40 retains its gradually sloped character from one cycle to the next when not covered by a maskant. This is to illustrate the consistent and uniform attack on the surface by the etchant solution. Highly sloped surface feature 44 again illustrates the effect of a highly stable maskant agglomeration while medium sloped surface feature 45 again demonstrates an intermediate condition. As illustrated in the second drawing of FIG. 3, four major surface levels are illustrated. Points at unetched level 46 are still apparent although fewer in number and relatively rare. A number of plateaus remain at first etched level 47 and second etched level 75. Those areas which have been exposed during all three etchant cycles enjoy depressions at third etched surface 100 corresponding to level D in FIG. 3. These levels correspond to areas which have had coverage during all three cycles, two cycles, one cycle and no cycles, respectively. The result as shown by third etched surface 90 is of a highly non-uniform featured surface which, compared with its length, also exhibits a large surface area. The different levels of depression and protrusion are particularly adapted to permit the ingrowth of bone and to allow for a firm anchoring of the bone along the surface of the implant structure.

Figure 4:
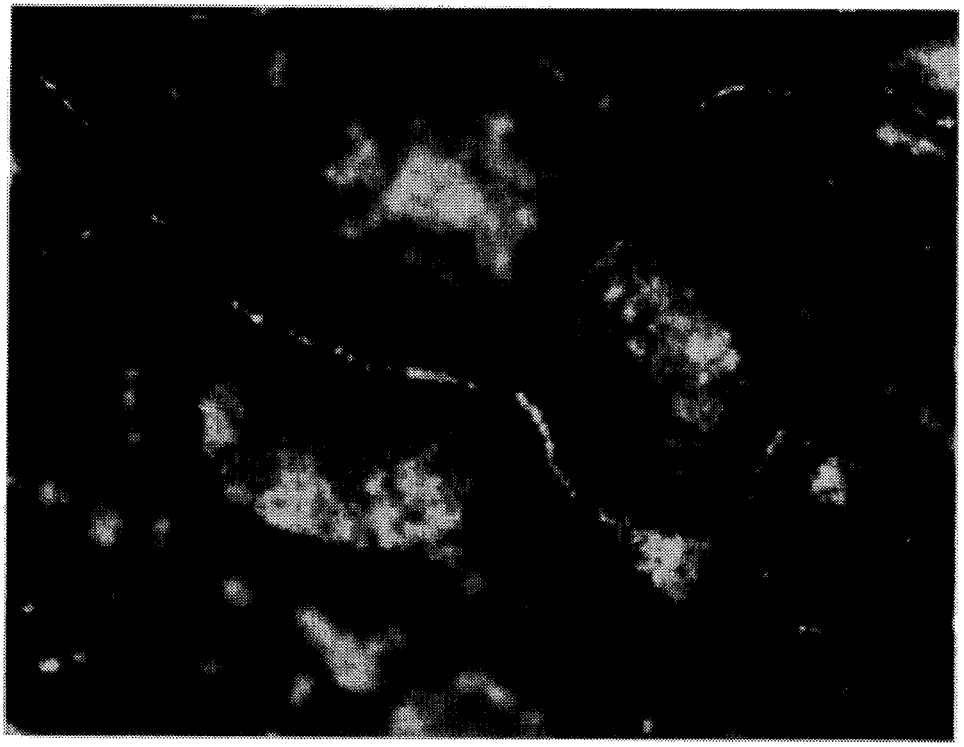
FIG. 4 is a photomicrograph of the surface.

FIG. 4 illustrates a sample resultant surface. While specific identification of the surface features is difficult, a long ridge line is visible extending diagonally from upper left to lower right. A first level of three plateaus is visible at the center of the Figure, and lower level features extend outwardly in the upper right and lower left directions. All surface features are fully filleted and irregularly shaped to promote bone ingrowth.

While a present preferred embodiment of the invention is described, it is to be distinctly understood that the invention is not limited thereto but may be otherwise embodied and practiced within the scope of the following claims.

What is claimed is:

1. A bone implant formed of a substrate material and having an exterior surface, a portion of said exterior surface being adapted to be joined to a segment of natural bone within the human body, the surface portion to be so joined comprising a plurality of randomly sized, as defined by height and thickness, and spaced, as defined by proximity therebetween, protrusions, which are unstressed with respect to said surface portion, located upon said surface portion in its entirety, said protrusions being formed of the bone implant substrate material and constructed monolithically therefrom.

2. A bone implant as described in claim 1, wherein said protrusions are generally perpendicular to said surface portion.

3. A bone implant as described in claim 1, wherein said protrusions join said substrate at fully dimensioned filleted radii.

4. A bone implant as described in claim 1, wherein said protrusions are formed in levels.

5. A bone implant as described in claim 4, wherein said levels each comprise a plurality of protrusions which are generally of the same height.

6. A bone implant as described in claim 5, further comprising a minority of protrusions which are of a height intermediate that of said levels.

7. A bone implant as described in claim 1, wherein each of said protrusions has at least one surface feature, said protrusions being distinguished by the varying slope of said at least one surface feature.

8. A bone implant as described in claim 7, wherein each of said protrusions has a plurality of sides of varying slope.

9. A bone implant formed of a substrate material and having an exterior surface, a portion of said exterior surface being adapted to be joined to a segment of natural bone within the human body, the surface portion to be so joined comprising a plurality of randomly sized, as defined by height and thickness, and spaced, as defined by proximity therebetween, protrusions, which are unstressed with respect to said surface portion, located upon said surface portion in its entirety, said protrusions being monolithically formed of the bone implant substrate material and constructed by:

a) masking said surface portion in a random pattern with a maskant material, such that less than the entire surface portion is covered thereby;

b) etching said surface portion utilizing a chemical agent such that said substrate material is removed thereby in areas uncovered by said maskant material, and areas covered by said maskant material are left intact;

c) removing said maskant material; and d) repeating said masking, etching and removing steps until a desired surface irregularity is achieved.

10. A bone implant as described in claim 9, wherein said protrusions are generally perpendicular to said surface portion.

11. A bone implant as described in claim 10, further comprising the additional step of randomly milling said substrate material from said surface portion.

12. A bone implant as described in claim 9, wherein said protrusions join said substrate at fully dimensioned filleted radii.

13. A bone implant as described in claim 12, wherein said random milling imparts no stress to said protrusions.

14. A bone implant as described in claim 9, wherein said protrusions are formed in levels.

15. A bone implant as described in claim 14, wherein said levels each comprise a plurality of protrusions which are generally of the same height.

16. A bone implant as described in claim 15, further comprising a minority of protrusions which are of a height intermediate that of said levels.

17. A bone implant as described in claim 9, wherein said protrusions incorporate a plurality of surface features.

18. A bone implant as described in claim 17, wherein said protrusions are distinguished by differing surface features thereon.

19. A bone implant as described in claim 17, wherein each of said protrusions has at least one surface feature, said protrusions being distinguished by the varying slope of said surface features.

20. A bone implant as described in claim 19, wherein each of said protrusions has a plurality of sides of varying slope.

* * * * *

UNITED STATES PATENT AND TRADEMARK OFFICE
CERTIFICATE OF CORRECTION

PATENT NO. : 5,507,815

DATED : April 16, 1996

INVENTOR(S) : Donald J. Wagner and Gary Reed

It is certified that error appears in the above-identified patent and that said Letters Patent is hereby corrected as shown below:

In the claims:

Column 8, line 29, "12" should be -- 11 --.

Signed and Sealed this

Seventh Day of January, 1997

Attest:

BRUCE LEHMAN

*Attesting Officer*    *Commissioner of Patents and Trademarks*